United States Patent
Borna Tutuc (10) Patent No.: US 10,132,765 B2
(45) Date of Patent: Nov. 20, 2018

(54) METHOD AND APPARATUS FOR DETERMINING LATTICE PARAMETERS OF A STRAINED III-V SEMICONDUCTOR LAYER

(71) Applicant: Infineon Technologies Austria AG, Villach (AT)

(72) Inventor: Marija Borna Tutuc, Villach (AT)

(73) Assignee: Infineon Technologies Austria AG, Villach (AT)

( * ) Notice: Subject to any disclaimer, the term of this patent is extended or adjusted under 35 U.S.C. 154(b) by 245 days.

(21) Appl. No.: 15/163,098

(22) Filed: May 24, 2016

(65) Prior Publication Data
US 2017/0343491 A1 Nov. 30, 2017

(51) Int. Cl.
*G01N 23/207* (2018.01)
*H01L 29/778* (2006.01)
*H01L 29/20* (2006.01)
*H01L 29/04* (2006.01)

(52) U.S. Cl.
CPC ..... *G01N 23/207* (2013.01); *G01N 2223/607* (2013.01); *G01N 2223/615* (2013.01); *G01N 2223/6116* (2013.01); *H01L 29/04* (2013.01); *H01L 29/2003* (2013.01); *H01L 29/7786* (2013.01)

(58) Field of Classification Search
CPC ........... G01N 2223/607; G01N 23/207; G01N 2223/611; G01N 2223/6116; G01N 2223/615; G01N 23/2055; G01N 2223/056; G01N 2223/601
See application file for complete search history.

(56) References Cited

U.S. PATENT DOCUMENTS

| | | | |
|---|---|---|---|
| 7,769,134 B1 * | 8/2010 | Adam | G01N 23/20 378/72 |
| 2012/0140889 A1 * | 6/2012 | Wall | G01N 23/207 378/73 |
| 2012/0146050 A1 * | 6/2012 | Adam | G01N 23/207 378/72 |
| 2017/0343491 A1 * | 11/2017 | Borna Tutuc | G01N 23/207 |

* cited by examiner

*Primary Examiner* — Glen Kao
(74) *Attorney, Agent, or Firm* — Murphy, Bilak & Homiller, PLLC (57) ABSTRACT

A multi-layer arrangement of III-V semiconductor layers includes a strained III-V semiconductor layer having a concentration of a constituent element which effects intensity of a conductive channel formed in the multi-layer arrangement. Lattice parameters of the strained III-V semiconductor layer are determined by generating a first scan in a Qx direction for a chosen reflection in reciprocal space based on diffracted X-Ray beam intensity measurements in the Qx direction. A second scan is generated in a Qz direction for the chosen reflection in the reciprocal space based on diffracted X-Ray beam intensity measurements in the Qz direction. The second scan is aligned with a diffracted X-Ray peak in the first scan which identifies the strained III-V semiconductor layer. The degree of strain of the strained III-V semiconductor layer is determined based on the first scan and the concentration of the constituent element based on the second scan.

19 Claims, 4 Drawing Sheets

METHOD AND APPARATUS FOR DETERMINING LATTICE PARAMETERS OF A STRAINED III-V SEMICONDUCTOR LAYER

TECHNICAL FIELD

The present application relates to III-V semiconductors, in particular to determining lattice parameters of a strained III-V semiconductor layer.

BACKGROUND

The GaN/Al$_x$Ga$_{(1-x)}$N HEMT (High Electron Mobility Transistor) concept is based on the formation of a 2-dimensional electron gas (2DEG) at the interface between GaN and Al$_x$Ga$_{(1-x)}$N. In general, for the formation of a 2DEG, two semiconductor materials with similar lattice constants but different band gaps are needed. At the interface between the two semiconductors e.g. GaN and Al$_x$Ga$_{(1-x)}$N, due to the different band gaps, there is a band bending phenomenon in which the conduction band energy minimum line (CB) of the large band gap semiconductor (e.g. GaN) is bent upwards, while the CB of the smaller band gap semiconductor (e.g. Al$_x$Ga$_{(1-x)}$N) is bent downwards. This phenomenon leads to the formation of a triangular potential well at the interface. If the minimum of the potential well is lower than the Fermi energy of the material, the potential well is populated by electrons that will be confined in the z-direction, therefore forming a 2-dimensional system. The degree to which the potential well is populated by electrons can be tuned by engineering the band gap of the Al$_x$Ga$_{(1-x)}$N.

The Al content in the Al$_x$Ga$_{(1-x)}$N barrier layer of a GaN/Al$_x$Ga$_{(1-x)}$N HEMT structure influences the electron density in the 2D electron gas (2DEG) and therefore defines the threshold voltage, breakthrough voltage, and other device parameters. The energy gap of Al$_x$Ga$_{(1-x)}$N is directly proportional to Al concentration. Therefore, Al concentration in the barrier layer should be a very well defined parameter with a very narrow process tolerance. For example, in the case of some GaN/Al$_x$Ga$_{(1-x)}$N HEMT devices, an epitaxial growth process tolerance of 1% is targeted for the Al content in the barrier layer. In terms of measurement, such an epitaxial growth process tolerance means that the measurement should be gage capable with a tolerance of 0.1%. In order to achieve such precision, a new measurement concept is needed.

Common for all HEMT structures is that they include a substrate which refers to epitaxial layers on which the barrier layer is grown, a spacer such as a thin AlN layer between GaN and Al$_x$Ga$_{(1-x)}$N and a barrier such as an Al$_x$Ga$_{(1-x)}$N layer. In the case of GaN HEMTs, the substrate can include many different multi epitaxial layer stacks such as consecutive Al$_x$Ga$_{(1-x)}$N layers with increasing thickness and decreasing Al content, a supperlattice such as alternating thin GaN and AlN layers, a structure with a back barrier layer like an additional Al$_x$Ga$_{(1-x)}$N layer with very small Al content, etc. Each type of substrate can be very different in terms of number of layers, layer thicknesses and compositions.

As HEMT structures consist of crystalline layers, a reliable way of measuring Al content in the barrier layer is by the use of HRXRD (High Resolution X-Ray Diffraction) methods. To precisely determine the Al content in the barrier layer of a HEMT structure, the lattice parameters must be determined first. In case of an epitaxial layer, lattice constants are defined, among others, by composition and strain or stress.

A conventional method commonly used is the so-called Omega-2Theta scans on 002, 004 and 006 reflections of a GaN/Al$_x$Ga$_{(1-x)}$N HEMT structure. The interpretation or analysis of these scans raises difficulties with low intensity peaks and peak overlaps that prevent precise lattice parameters determination. These scans are 1-dimensional scans that cannot resolve the influence of the composition and strain on the lattice parameters, and therefore strain must be assumed to be constant and maximal (100%), which introduces further error in the Al content determination. Omega-2Theta scans therefore provide only qualitative data, but not the absolute values of Al content in the barrier layer. During the fitting of 002, 004 and 006 Omega-2Theta scans, the Al concentration in the barrier is fitted together with many other parameters (in total >10). The error introduced due to the very low intensity and overlapping of the barrier layer peak, together with assumptions on the strain of this layer, is very large and prevents this method from delivering the necessary precision for determining the Al concentration in the barrier layer.

Another conventional approach for qualitative determination of the Al content in the Al$_x$Ga$_{(1-x)}$N barrier layer of a GaN/Al$_x$Ga$_{(1-x)}$N HEMT structure is photo-luminescence spectroscopy with a 266 nm laser. This method provides information on the electronic structure of materials, and indirectly on Al composition. However, the photo-luminescence spectroscopy method does not account for strain. The accuracy and precision of the photo-luminescence spectroscopy method is lower than in the case of Omega-2Theta scans.

Accordingly, there is a need for more precisely determining lattice parameters of the barrier layer of a HEMT structure.

SUMMARY

According to an embodiment, a method of determining lattice parameters of a strained III-V semiconductor layer of a multi-layer arrangement of III-V semiconductor layers is provided. The strained III-V semiconductor layer has a concentration of a constituent element which effects intensity of a conductive channel formed in the multi-layer arrangement. The method comprises: generating a first scan of the multi-layer arrangement in a Qx direction for a chosen reflection in reciprocal space based on diffracted X-Ray beam intensity measurements in the Qx direction, the reciprocal space describing positions of diffracted X-Ray peaks of the III-V semiconductor layers with respect to one another; generating a second scan of the multi-layer arrangement in a Qz direction for the chosen reflection in in the reciprocal space based on diffracted X-Ray beam intensity measurements in the Qz direction, the second scan being aligned with a diffracted X-Ray peak in the first scan which identifies the strained III-V semiconductor layer; and determining a degree of strain of the strained III-V semiconductor layer based on the first scan and the concentration of the constituent element based on the second scan.

According to an embodiment of a corresponding X-Ray diffraction apparatus, the X-Ray diffraction apparatus comprises an adjustable stage configured to receive the multi-layer arrangement, an X-Ray source configured to direct an incident X-Ray beam at a surface of the multi-layer arrangement, a detector configured to measure intensity of the diffracted X-Ray beam, and a control system. The control system is configured to: control angular position of the surface of the multi-layer arrangement relative to the adjustable stage, the X-Ray source and the detector; generate a first scan of the multi-layer arrangement in a Qx direction for a chosen reflection in reciprocal space based on diffracted X-Ray beam intensity measurements in the Qx direction, the reciprocal space describing positions of diffracted X-Ray peaks of the III-V semiconductor layers with respect to one another; generate a second scan of the multi-layer arrangement in a Qz direction for the chosen reflection in in the reciprocal space based on diffracted X-Ray beam intensity measurements in the Qz direction, the second scan being aligned with a diffracted X-Ray peak in the first scan which identifies the strained III-V semiconductor layer; and determine a degree of strain of the strained III-V semiconductor layer based on the first scan and the concentration of the constituent element based on the second scan.

Those skilled in the art will recognize additional features and advantages upon reading the following detailed description, and upon viewing the accompanying drawings.

BRIEF DESCRIPTION OF THE FIGURES

The elements of the drawings are not necessarily to scale relative to each other. Like reference numerals designate corresponding similar parts. The features of the various illustrated embodiments can be combined unless they exclude each other. Embodiments are depicted in the drawings and are detailed in the description which follows.

DETAILED DESCRIPTION

Embodiments described herein provide a method and apparatus for high precision and high accuracy measurement of lattice parameters, Al content and strain determination in the $Al_xGa_{(1-x)}N$ barrier layer in a multi-epitaxial-layer structure of a $GaN/Al_xGa_{(1-x)}N$ HEMT by using Qz scan with alignment in a Qx direction on an asymmetric reflection. The metrology solution described herein decouples layer composition and strain and provides for very precise and highly accurate determination of Al content. In addition to Al concentration, layer strain is another important parameter for $GaN/Al_xGa_{(1-x)}N$ HEMT devices which can be precisely and accurately measured using the metrology solution described herein.

In general, the metrology solution described herein can be used with any III-V material system in which a strained III-V semiconductor layer of a multi-layer arrangement of III-V semiconductor layers has a concentration of a constituent element such as Al, In, etc. which effects intensity of the conductive channel formed in the multi-layer arrangement. The metrology solution described herein can be used to determine the lattice parameters of such a strained III-V semiconductor layer, which in turn can be used to determine the degree of strain and constituent element concentration of the layer.

Figure 1:
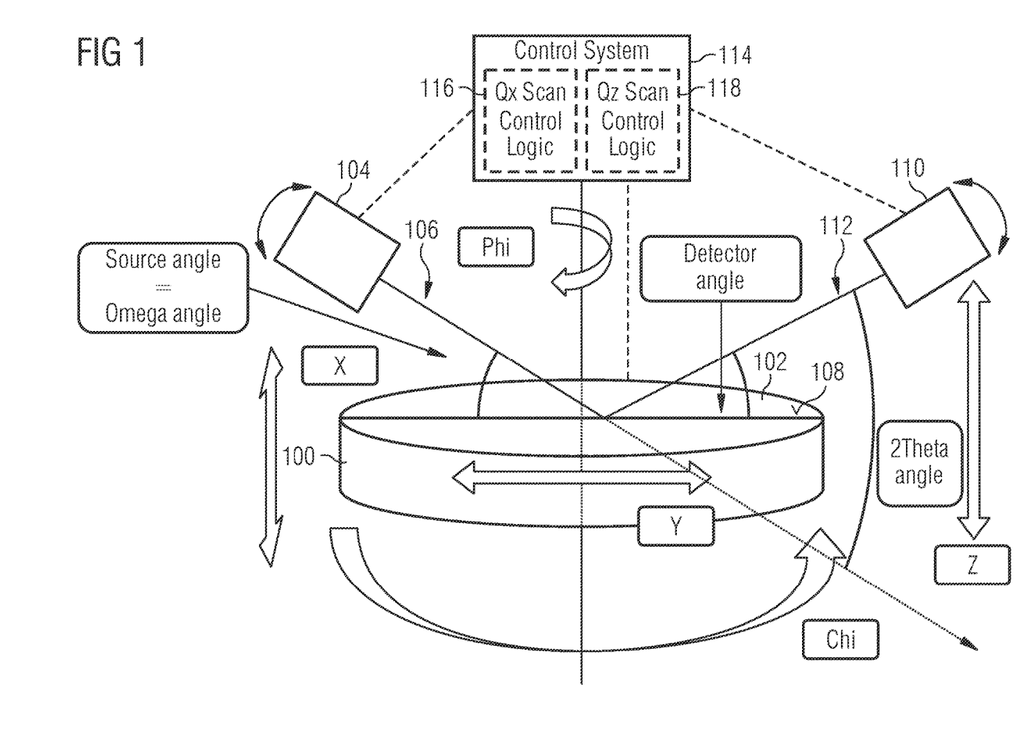
FIG. 1 illustrates a block diagram representation of an embodiment of an HRXRD (High Resolution X-Ray Diffraction) apparatus designed for determining lattice parameters of a strained III-V semiconductor layer of a III-V multi-layer sample.

FIG. 1 illustrates an embodiment of an HRXRD (High Resolution X-Ray Diffraction) apparatus designed for determining lattice parameters of a strained III-V semiconductor layer of a multi-layer arrangement of III-V semiconductor layers, the strained III-V semiconductor layer having a concentration of a constituent element such as Al, In, etc. which effects intensity of a conductive channel formed in the multi-layer arrangement. The HRXRD apparatus comprises an adjustable stage 100 for receiving a III-V multi-layer sample 102, an X-Ray source 104 for directing an incident X-Ray beam 106 at a surface 108 of the III-V multi-layer sample 102, a detector 110 for measuring intensity of the diffracted X-Ray beam 112, and a control system 114 for controlling angular position of the surface 108 of the III-V multi-layer sample 102 relative to the adjustable stage 100, the X-Ray source 104 and the detector 110. For example, the control system 114 can adjust the X-Ray source angle (Omega) and the detector angle (and therefore the 2Theta angle) relative to the surface 108 of the III-V multi-layer sample 102. The control system 114 can also adjust the x, y and z position of the stage 100 relative to the X-Ray source 104 and the detector 110, as well as rotational angle Phi ($\phi$) and tilt angle Chi ($\chi$) of the stage 100 relative to the incident and diffracted X-Ray beams 106, 112.

The control system 114 of the HRXRD apparatus can be implemented as a computer system such as a PC (personal computer), tablet computer, server, etc. which is in communication with the adjustable stage 100, the X-Ray source 104 and the detector 110. Communication can be enabled over wired buses or links, over one or more wireless channels or some combination of both. The control system 114 comprises one or more processing circuits such as one or more controllers, processors, ASICs (application-specific integrated circuits), etc. for executing program code which performs the metrology functions described herein. To this end, Qx scan control logic 116 and Qz scan control logic 118 are included in or associated with the processing circuitry of the control system 114 for performing the metrology functions. The control system 114 can also include one or more storage media such as DRAM (dynamic random access memory) and an HDD (hard disk drive) and/or other mass storage device for storing the program code and related data processed and accessed by the processing circuitry, including the Qx and Qz scan control logic 116, 118, during execution of program code. The storage medium also stores the results generated by the control system 114.

By appropriately controlling the angular position of the surface 108 of the III-V multi-layer sample 100 relative to the adjustable stage 100, the X-Ray source 104 and the detector 110 of the HRXRD apparatus, the control system 114 can determine the lattice parameters of a strained III-V semiconductor layer included in the multi-layer sample 102 received by the stage 100, which in turn can be used to determine the degree of strain and constituent element concentration of the strained layer. The III-V multi-layer sample 102 received by the stage 100 can be a III-V semiconductor chip, a III-V semiconductor wafer, etc.

Figure 2:
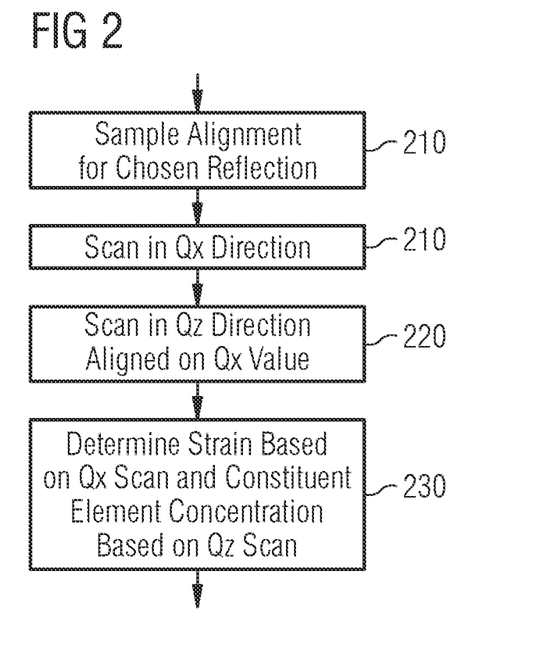
FIG. 2 illustrates a flow diagram of an embodiment of a method of determining lattice parameters of a strained III-V semiconductor layer of a III-V multi-layer sample.

Operation of the control system 114 is described next with reference to FIG. 2, which illustrates a flow diagram of the metrology process.

The control system 114 aligns the multi-layer sample 102 with the X-Ray source 104 and the detector 110 of the HRXRD apparatus so as to satisfy Bragg equations for a chosen (predefined) reflection of the III-V binary channel layer such as the (1, 1, 4) reflection for GaN (Block 200). The Qx scan control logic 116 of the control system 114 then generates a scan of the III-V multi-layer sample 100 in the Qx direction for a chosen reflection in reciprocal space based on diffracted X-Ray beam intensity measurements in the Qx direction (Block 210). The reciprocal space projects the real space of a crystal lattice of the sample 100 to the q-space, and describes positions of the III-V semiconductor layers with respect to one another in the q-space. Diffracted peak position in the Qx direction correlates to the strain in the respective layer. Use of an asymmetric reflection with high sum of h+l+l allows for peak separation and therefore observation of planes which are not parallel or nearly parallel to the surface 108 of the sample 102. In HRXRD, the range of accessible reflections in the q-space can be increased by using X-Rays of a higher energy and the structure factor of the crystal determines the diffracted X-Ray beam intensity.

The Qz scan control logic 118 of the control system 114 generates a scan of the III-V multi-layer sample 100 in the Qz direction for the chosen reflection in the reciprocal space based on diffracted X-Ray beam intensity measurements in the Qz direction (Block 220). Position in the Qz direction correlates to the d-spacing of the peak, where the diffraction space coordinates are defined as Qx, Qy and Qz. The control system 114 aligns the scan in the Qz direction with a diffracted X-Ray peak in the Qx scan which corresponds to the strained III-V semiconductor layer. This way, the scan in the Qz direction is aligned on the strained III-V semiconductor layer of interest in the Qx direction. The control system 114 determines the degree of strain of the III-V semiconductor layer of interest based on the Qx scan, and determines the concentration of the constituent element (e.g. Al, In, etc.) based on the Qz scan (Block 230). All diffracted X-Ray beam intensity measurements are taken by the detector 110 of the HRXRD apparatus and analyzed by the control system 114 to identify the diffracted X-Ray peaks in the Qx and Qz directions of the reciprocal space.

By aligning for the Qz scan in the Qx direction, peak separation and simultaneous determination of the constituent element (e.g. Al, In, etc.) concentration in the strained III-V semiconductor layer of interest and degree of strain of that layer can be obtained. In more detail, a Qz scan in HRXRD means a linear scan in a reciprocal space in the Qz direction. The Qz scan can be performed on a symmetric or asymmetric reflection. For example, on a well-chosen asymmetric reflection such as (1, 1, 4) for GaN, the Qz scan allows for clear separation of the barrier layer peak from the remaining peaks of the same structure and, at the same time, being a 2-dimensional scan in combination with the Qx scan, allows for determination of the degree of strain in the barrier layer. To precisely measure the concentration of the constituent element (e.g. Al, In, etc.) which effects intensity of the conductive channel formed in the III-V multi-layer sample 100, an additional alignment step is performed by the control system 114 in the Qx direction. This alignment step ensures that the Qz scan is through the peak maximum, enabling a highly accurate and precise method for determining constituent element concentration of a strained barrier layer. Information about the strain of the barrier layer can be obtained by the peak position in the Qx direction.

For GaN/Al$_x$Ga$_{(1-x)}$N HEMT structures, the barrier layer comprises Al$_x$Ga$_{(1-x)}$N and becomes strained during epitaxial growth. In case that barrier layer is 100% strained, the peak originating from the barrier layer falls on the same Qx position as the GaN peak in the reciprocal space map for an asymmetric reflection. As such, there is no offset between the centerlines of the peaks. However, in case of partial relaxation i.e. less than 100% strain of the barrier layer, the peak shifts toward larger values in the Qx direction. The degree of strain can be precisely determined based on the amount of offset between the centerlines of the two peaks. However, to ensure that the Qz scan is done through the maximum of the barrier layer peak, an additional alignment step in the Qx direction is performed.

From the position of the barrier layer peak in the Qx direction, the strain in the barrier layer can be determined. Due to a clear peak separation, the constituent element (e.g. Al, In, etc.) concentration can be refined as the only parameter from the barrier layer peak position in the Qz direction. This method can be used to precisely determine the constituent element concentration and strain of the barrier layer for many different substrate structures. This method can be applied to all GaN epitaxy based products, and more generally to any III-V material systems in which a strained III-V semiconductor layer of a multi-layer arrangement of III-V semiconductor layers has a concentration of a constituent element which effects intensity of the conductive channel formed in the multi-layer arrangement. For example, the method could be used to determine the strain and In concentration of an InAlGaN barrier layer of a GaN HEMT structure in which the strain and In content of the InAlGaN barrier layer effect the intensity of the conductive channel. Different reflections can be chosen and changes in alignment can be made based on the particular III-V material system under consideration.

The metrology solution is described next in further detail in connection with the exemplary III-V material system illustrated in FIG. 3, which is provided only for illustrative purposes and should not be considered limiting in any way. The exemplary III-V material system includes a Si growth substrate, an AlN nucleation layer, several transition layers (TL1-TL4) such as Al$_x$Ga$_{(1-x)}$N layers of varying thickness and Al concentration, a binary III-V channel layer such as GaN and a ternary III-V barrier layer such as Al$_x$Ga$_{(1-x)}$N. Specifically with regard to GaN technology, the presence of polarization charges and strain effects in a GaN-based heterostructure body due to spontaneous and piezoelectric polarization yield a two-dimensional charge carrier gas in the heterostructure body characterized by very high carrier density and carrier mobility. This two-dimensional charge carrier gas, such as a 2DEG (two-dimensional electron gas) or 2DHG (two-dimensional hole gas), forms a conductive channel near the interface between the barrier layer such as 'AlGaN', 'InAlGaN', 'InAlN', etc. and the underlying GaN channel layer. A thin, e.g. 1-2 nm, AlN layer can be provided between the GaN channel layer and the barrier layer to minimize alloy scattering and enhance 2DEG mobility. A capping layer such as a layer of GaN can be formed on the barrier layer.

In a broad sense, the III-V multi-layer arrangements described herein can be formed from any binary, ternary or quaternary III-nitride compound semiconductor material where piezoelectric effects are responsible for the device concept. Any suitable growth substrate such as Si, SiC or sapphire can be used. In the case of a Si growth substrate, a nucleation (seed) layer such as AlN can be formed for preventing chemical reaction between Si and Ga and for decreasing the lattice mismatch to the overlying III-V layers. 'AlInN/AlN/GaN' barrier/spacer/buffer layer structures can also be included in the III-V material stack. In general, the III-V multi-layer arrangements described herein can be realized using any suitable III-V technology such as GaAs, GaN, etc.

Figure 3:
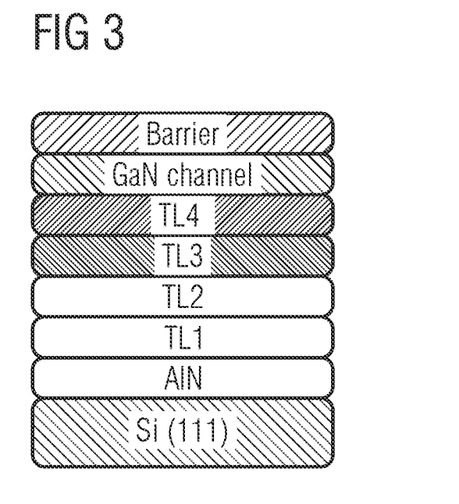
FIG. 3 illustrates a sectional view of an exemplary III-V material system having a strained III-V semiconductor layer for which the lattice parameters are to be determined using the method of FIG. 2 and the HRXRD apparatus of FIG. 1.

Returning to the III-V multi-layer arrangement example shown in FIG. 3, the strain and constituent element (e.g. Al, In, etc.) concentration of the ternary III-V barrier layer effect intensity of the conductive channel formed in the multi-layer arrangement. The strain and constituent element concentration of the III-V ternary barrier layer can be derived from the barrier layer lattice parameters, which are initially unknown because the exact degree of stress and constituent element concentration for the barrier layer are not known.

To generate the first scan in the Qx direction, the control system 114 aligns the exemplary multi-layer arrangement shown in FIG. 3 with the X-Ray source 104 and the detector 110 of the HRXRD apparatus so as to satisfy Bragg equations for a chosen (predefined) reflection of the III-V binary channel layer such as the (1, 1, 4) reflection for GaN. Because the III-V channel layer is a binary compound with well-defined lattice parameters, the Bragg equations can be readily solved.

As part of the scanning process in the Qx direction for the chosen reflection, the control system 114 changes one or more of the angles Omega, 2Theta, Chi and/or Phi while an incident X-Ray beam is directed at the surface of the multi-layer arrangement. As a result, a plurality of diffracted X-Ray peaks can be produced in the Qx direction for a nominal constituent element composition. The X-Ray peaks in the Qx direction are detected by the detector 110 and identify the different III-V semiconductor layers in the multi-layer arrangement.

Figure 4:
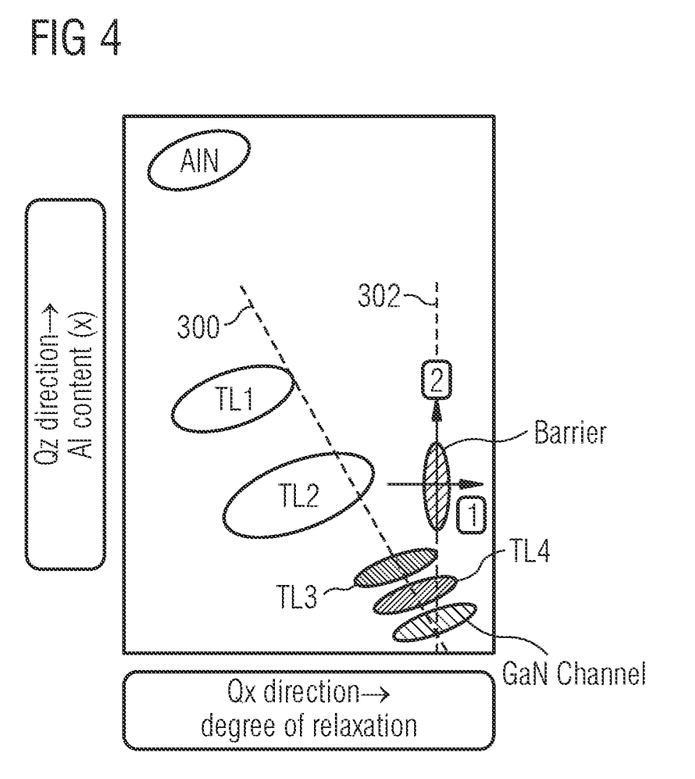
FIG. 4 illustrates a pictorial representation of scanning results for a RSM (reciprocal space map) scan for the exemplary sample of FIG. 3, in which Qx and Qz directions are shown.

FIG. 4 illustrates a pictorial representation of scanning result for a RSM (reciprocal space map) scan for the exemplary sample of FIG. 3. Qx and Qz directions are shown. Each oval shown in FIG. 4 corresponds to a diffracted X-Ray peak detected by the detector 110. Each diffracted X-Ray peak represents one III-V semiconductor layer in the exemplary multi-layer arrangement shown in FIG. 3. The diffracted X-Ray peak corresponding to the III-V binary channel layer is easily identified, because its lattice parameters are known as explained above. Using the diffracted X-Ray peak corresponding to the III-V binary channel layer as a point of reference, the other III-V semiconductor layers in the multi-layer arrangement can be identified based on the other diffracted X-Ray peaks. This includes identifying the ternary III-V barrier layer of interest. Each III-V semiconductor layer of the multi-layer arrangement is labeled in FIG. 4 to indicate its position in the q-space map. The scan through the ternary III-V barrier layer in the Qx direction is represented by the solid line labeled '1' in FIG. 4.

The degree of strain of the ternary III-V barrier layer is determined by comparing the hypothetical diffracted peak position on the centerline 300 for the same Qz nominal value X-Ray to the centerline 302 of the diffracted X-Ray peak which identifies the ternary III-V barrier. The difference between the centerlines 300, 302 indicates the degree of strain of the ternary III-V barrier, which can be readily derived based on standard lattice equations.

FIG. 4 also illustrates the results of the scan in the Qz direction, which is performed by aligning the X-Ray source 104 and the detector 110 of the HRXRD apparatus on the diffracted X-Ray peak position which identifies the ternary III-V barrier layer in the Qx direction. This peak is labeled 'Barrier' in FIG. 4. An incident X-Ray beam is then directed at the surface of the exemplary multi-layer arrangement while aligned on the diffracted X-Ray peak which identifies the ternary III-V barrier layer in the Qx direction. Performing the scan in the Qz direction while aligned on the diffracted X-Ray peak for the ternary III-V barrier layer in the Qx direction produces a diffracted X-Ray peak only for the barrier layer in the Qz direction. The scan through the ternary III-V barrier layer in the Qz direction is represented by the solid line labeled '2' in FIG. 4.

The concentration of the constituent element (e.g. Al, In, etc.) in the ternary III-V barrier layer is determined based on the scan in the Qz direction, by identifying a position of the maximum of the sole scattered X-Ray peak in the Qz direction. Provided there is a sufficient level of peak separation for the chosen reflection, by aligning on the diffracted X-Ray peak for the ternary III-V barrier layer in the Qx direction, the only diffracted X-Ray peak produced in the Qz direction corresponds to the ternary III-V barrier layer of interest. As such, the Al concentration of the ternary III-V barrier layer can be precisely determined based on standard lattice equations by identifying the maximum of the single scattered X-Ray peak observed in the Qz direction.

Specifically for a HEMT which includes an $Al_xGa_{(1-x)}N$ barrier layer adjoining a GaN channel layer, the degree of strain of the $Al_xGa_{(1-x)}N$ barrier layer is determined by identifying the diffracted X-Ray peak in the Qx scan which corresponds to the GaN buffer layer and identifying the diffracted X-Ray peak in the Qx scan which corresponds to the $Al_xGa_{(1-x)}N$ barrier layer. The difference between the centerlines of the two diffracted X-Ray peaks in the Qx scan indicates the degree of strain of the $Al_xGa_{(1-x)}N$ barrier layer as explained above. Al concentration of the $Al_xGa_{(1-x)}N$ barrier layer is determined by identifying the maximum of the only diffracted X-Ray peak in the Qz scan (provided a sufficient level of peak separation for the chosen reflection), which corresponds to the $Al_xGa_{(1-x)}N$ barrier layer also as explained above. The scan in the Qz direction is aligned on the diffracted X-Ray peak for the $Al_xGa_{(1-x)}N$ barrier layer in the Qx direction so as to produce a single diffracted X-Ray peak in the Qz direction which corresponds to the $Al_xGa_{(1-x)}N$ barrier layer of interest.

Figure 5:
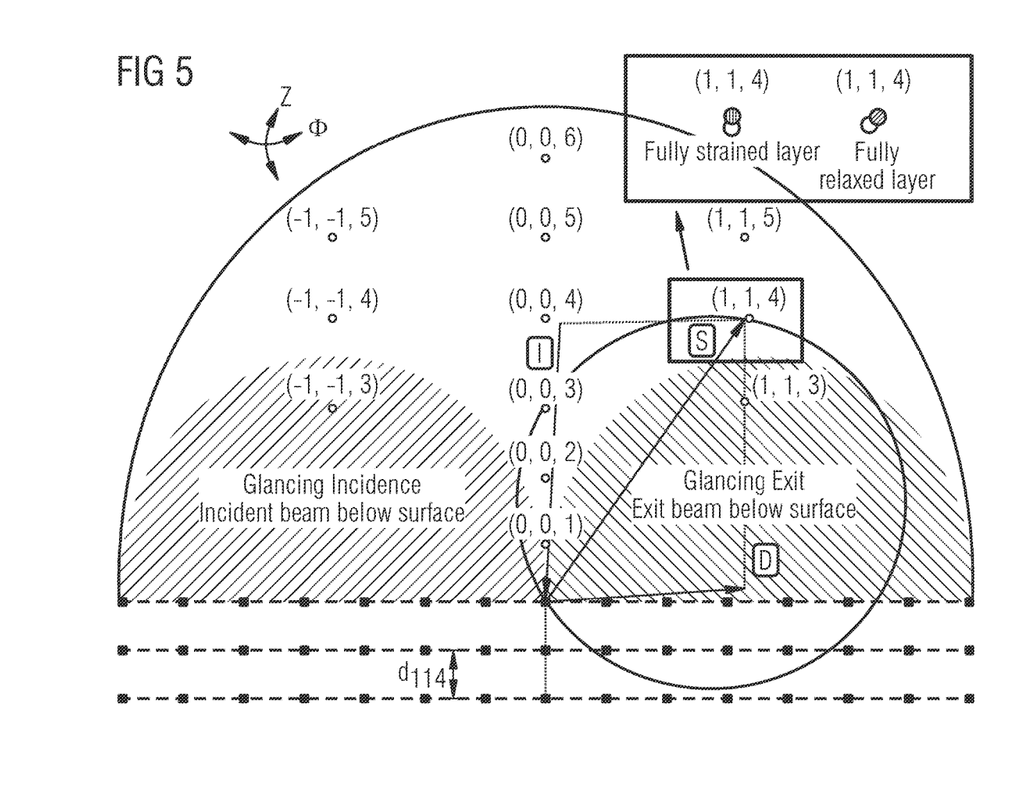
FIG. 5 illustrates a pictorial representation of an exemplary q-space map in a reciprocal space for a sample having an $Al_xGa_{(1-x)}N$ barrier layer and a GaN channel layer.

FIG. 5 illustrates an exemplary q-space map (the Ewald sphere) for an exemplary sample having an $Al_xGa_{(1-x)}N$ barrier layer and a GaN channel layer. The q-space map shown in FIG. 5 represents a section through a reciprocal space for a [001] oriented GaN layer. Inaccessible regions are labeled 'Glancing Incidence' and 'Glancing Exit', which correspond to regions where the sample blocks the X-Ray beam. Vectors I and D have length $1/\lambda$ where $\Delta=1.54$ Å ($CuK\alpha_1$). The vector S is perpendicular to the (1, 1, 4) plane and has length of d(114). The Ewald sphere, which is a geometric construct used in electron, neutron, and X-Ray crystallography to demonstrate the relationship between the wave vector of the incident and diffracted X-Ray beams, the diffraction angle for a given reflection, and the reciprocal lattice of the crystal, is shown in FIG. 5 as a half-circle. Only the spots which have intensity higher than zero are shown. Planes of atoms are indicated by dotted lines, and are not necessarily parallel to the sample surface. The exploded view depicts the (1, 1, 4) spot of GaN and $Al_xGa_{(1-x)}N$ fully relaxed and fully strained, where $x=0.2$ in this example. The metrology approach described above can identify precisely the strain an Al concentration of the $Al_xGa_{(1-x)}N$ barrier layer.

Spatially relative terms such as "under", "below", "lower", "over", "upper" and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open-ended terms that indicate the presence of stated elements or features, but do not preclude additional elements or features. The articles "a", "an" and "the" are intended to include the plural as well as the singular, unless the context clearly indicates otherwise.

With the above range of variations and applications in mind, it should be understood that the present invention is not limited by the foregoing description, nor is it limited by the accompanying drawings. Instead, the present invention is limited only by the following claims and their legal equivalents.

What is claimed is:

1. A method of determining lattice parameters of a strained III-V semiconductor layer of a multi-layer arrangement of III-V semiconductor layers, the strained III-V semiconductor layer having a concentration of a constituent element which effects intensity of a conductive channel formed in the multi-layer arrangement, the method comprising:
   generating a first scan of the multi-layer arrangement in a Qx direction for a chosen reflection in reciprocal space based on diffracted X-Ray beam intensity measurements in the Qx direction, the reciprocal space describing positions of diffracted X-Ray peaks of the III-V semiconductor layers with respect to one another;
   generating a second scan of the multi-layer arrangement in a Qz direction for the chosen reflection in the reciprocal space based on diffracted X-Ray beam intensity measurements in the Qz direction, the second scan being aligned with a diffracted X-Ray peak in the first scan which identifies the strained III-V semiconductor layer;
   determining a degree of strain of the strained III-V semiconductor layer based on the first scan; and
   determining the concentration of the constituent element based on the second scan.

2. The method of claim 1, wherein the first and second scans are generated using an X-Ray diffraction apparatus which includes an adjustable stage for receiving the multi-layer arrangement, an X-Ray source for directing an incident X-Ray beam at a surface of the multi-layer arrangement, and a detector for measuring intensity of the diffracted X-Ray beam.

3. The method of claim 2, wherein the strained III-V semiconductor layer is a strained ternary III-V semiconductor layer and wherein generating the first scan in the Qx direction comprises:
   aligning the multi-layer arrangement with the X-Ray source and the detector so as to satisfy Bragg equations for a chosen reflection of a binary III-V semiconductor layer of the multi-layer arrangement, the binary III-V semiconductor layer having known lattice parameters; and
   changing angles between the surface of the multi-layer arrangement and the X-Ray source and the detector while directing the incident X-Ray beam at the surface of the multi-layer arrangement, so as to produce a plurality of diffracted X-Ray peaks in the Qx direction which identify different ones of the III-V semiconductor layers in the multi-layer arrangement.

4. The method of claim 3, wherein the binary III-V semiconductor layer is a GaN layer, and wherein the chosen reflection is a (1, 1, 4) reflection of the GaN layer.

5. The method of claim 3, wherein determining the degree of strain of the strained III-V semiconductor layer based on the first scan comprises:
   comparing a centerline of the diffracted X-Ray peak which identifies the binary III-V semiconductor layer to a centerline of the diffracted X-Ray peak which identifies the ternary III-V semiconductor layer, the difference between the centerlines indicating the degree of strain of the ternary III-V semiconductor layer.

6. The method of claim 3, wherein generating the second scan in the Qz direction comprises:
   aligning the X-Ray source and the detector on the diffracted X-Ray peak which identifies the ternary III-V semiconductor layer in the Qx direction; and
   directing the incident X-Ray beam at the surface of the multi-layer arrangement while aligned on the diffracted X-Ray peak which identifies the ternary III-V semiconductor layer in the Qx direction, so as to produce a diffracted X-Ray peak for the ternary III-V semiconductor layer in the Qz direction.

7. The method of claim 6, wherein determining the concentration of the constituent element based on the second scan comprises:
   identifying a position of the maximum of a scattered X-Ray peak for the ternary III-V semiconductor layer in the Qz direction.

8. The method of claim 1, wherein the multi-layer arrangement forms a HEMT (high-electron mobility transistor) structure, and wherein the strained III-V semiconductor layer is an $Al_xGa_{(1-x)}N$ barrier layer which adjoins a GaN buffer layer.

9. The method of claim 8, wherein determining the degree of strain of the strained III-V semiconductor layer based on the first scan comprises:
   identifying a first diffracted X-Ray peak in the first scan which corresponds to the GaN buffer layer;
   identifying a second diffracted X-Ray peak in the first scan which corresponds to the $Al_xGa_{(1-x)}N$ barrier layer; and
   comparing a centerline of the first diffracted X-Ray peak to a centerline of the second diffracted X-Ray peak, the difference between the centerlines indicating the degree of strain of the $Al_xGa_{(1-x)}N$ barrier layer.

10. The method of claim 8, wherein determining the concentration of the constituent element based on the second scan comprises:
    identifying the maximum of a diffracted X-Ray peak in the second scan which corresponds to the $Al_xGa_{(1-x)}N$ barrier layer.

11. An X-Ray diffraction apparatus designed for determining lattice parameters of a strained III-V semiconductor layer of a multi-layer arrangement of III-V semiconductor layers, the strained III-V semiconductor layer having a concentration of a constituent element which effects intensity of a conductive channel formed in the multi-layer arrangement, the X-Ray diffraction apparatus comprising:
    an adjustable stage configured to receive the multi-layer arrangement;

an X-Ray source configured to direct an incident X-Ray beam at a surface of the multi-layer arrangement;

a detector configured to measure intensity of a diffracted X-Ray beam; and a control system configured to:

control angular position of the surface of the multi-layer arrangement relative to the adjustable stage, the X-Ray source and the detector;

generate a first scan of the multi-layer arrangement in a Qx direction for a chosen reflection in reciprocal space based on diffracted X-Ray beam intensity measurements in the Qx direction, the reciprocal space describing positions of diffracted X-Ray peaks of the III-V semiconductor layers with respect to one another;

generate a second scan of the multi-layer arrangement in a Qz direction for the chosen reflection in the reciprocal space based on diffracted X-Ray beam intensity measurements in the Qz direction, the second scan being aligned with a diffracted X-Ray peak in the first scan which identifies the strained III-V semiconductor layer;

determine a degree of strain of the strained III-V semiconductor layer based on the first scan; and determine the concentration of the constituent element based on the second scan.

12. The X-Ray diffraction apparatus of claim 11, wherein the strained III-V semiconductor layer is a ternary III-V semiconductor layer and wherein the control system is configured to generate the first scan in the Qx direction by aligning the multi-layer arrangement with the X-Ray source and the detector so as to satisfy Bragg equations for a chosen reflection of a binary III-V semiconductor layer of the multi-layer arrangement, the binary III-V semiconductor layer having known lattice parameters, and changing angles between the surface of the multi-layer arrangement and the X-Ray source and the detector while directing the incident X-Ray beam at the surface of the multi-layer arrangement, so as to produce a plurality of diffracted X-Ray peaks in the Qx direction which identify different ones of the III-V semiconductor layers in the multi-layer arrangement.

13. The X-Ray diffraction apparatus of claim 12, wherein the binary III-V semiconductor layer is a GaN layer, and wherein the chosen reflection is a (1, 1, 4) reflection of the GaN layer.

14. The X-Ray diffraction apparatus of claim 12, wherein the control system is configured to determine the degree of strain of the strained III-V semiconductor layer based on the first scan by comparing a centerline of the diffracted X-Ray peak which identifies the binary III-V semiconductor layer to a centerline of the diffracted X-Ray peak which identifies the ternary III-V semiconductor layer, the difference between the centerlines indicating the degree of strain of the ternary III-V semiconductor layer.

15. The X-Ray diffraction apparatus of claim 12, wherein the control system is configured to generate the second scan in the Qz direction by aligning the X-Ray source and the detector on the diffracted X-Ray peak which identifies the ternary III-V semiconductor layer in the Qx direction, and directing the incident X-Ray beam at the surface of the multi-layer arrangement while aligned on the diffracted X-Ray peak which identifies the ternary III-V semiconductor layer in the Qx direction, so as to produce a diffracted X-Ray peak for the ternary III-V semiconductor layer in the Qz direction.

16. The X-Ray diffraction apparatus of claim 15, wherein the control system is configured to determine the concentration of the constituent element based on the second scan by identifying a position of the maximum of a scattered X-Ray peak for the ternary III-V semiconductor layer in the Qz direction.

17. The X-Ray diffraction apparatus of claim 11, wherein the multi-layer arrangement forms a HEMT (high-electron mobility transistor) structure, and wherein the strained III-V semiconductor layer is an $Al_xGa_{(1-x)}N$ barrier layer which adjoins a GaN buffer layer.

18. The X-Ray diffraction apparatus of claim 17, wherein the control system is configured to determine the degree of strain of the strained III-V semiconductor layer based on the first scan by identifying a first diffracted X-Ray peak in the first scan which corresponds to the GaN buffer layer, identifying a second diffracted X-Ray peak in the first scan which corresponds to the $Al_xGa_{(1-x)}N$ barrier layer, and comparing a centerline of the first diffracted X-Ray peak to a centerline of the second diffracted X-Ray peak, the difference between the centerlines indicating the degree of strain of the $Al_xGa_{(1-x)}N$ barrier layer.

19. The X-Ray diffraction apparatus of claim 17, wherein the control system is configured to determine the concentration of the constituent element based on the second scan by identifying the maximum of a diffracted X-Ray peak in the second scan which corresponds to the $Al_xGa_{(1-x)}N$ barrier layer.

* * * * *